United States Patent
Schunck et al.

(10) Patent No.: US 12,427,519 B2
(45) Date of Patent: Sep. 30, 2025

(54) MICROFLUIDIC DEVICE AND METHOD FOR SEPARATING OFF BLOOD SERUM

(71) Applicant: FRAUNHOFER-GESELLSCHAFT ZUR FÖRDERUNG DER ANGEWANDTEN FORSCHUNG E.V., Munich (DE)

(72) Inventors: Tobias Schunck, Karlsruhe (DE); Michael Bassler, Mainz (DE); Peter Spang, Gau-Bickelheim (DE)

(73) Assignee: Fraunhofer-Gesellschaft zur Förderung der Angewandten Forschung E.V., Munich (DE)

( * ) Notice: Subject to any disclaimer, the term of this patent is extended or adjusted under 35 U.S.C. 154(b) by 0 days.

(21) Appl. No.: 17/428,694

(22) PCT Filed: Jan. 31, 2020

(86) PCT No.: PCT/EP2020/052424
§ 371 (c)(1),
(2) Date: Aug. 5, 2021

(87) PCT Pub. No.: WO2020/161013
PCT Pub. Date: Aug. 13, 2020

(65) Prior Publication Data
US 2022/0097061 A1 Mar. 31, 2022

(30) Foreign Application Priority Data
Feb. 5, 2019 (DE) .................. 102019102822.1

(51) Int. Cl.
*B01L 3/00* (2006.01)
*G01N 33/49* (2006.01)

(52) U.S. Cl.
CPC ... *B01L 3/502753* (2013.01); *B01L 3/502746* (2013.01); *G01N 33/491* (2013.01);
(Continued)

(58) Field of Classification Search
CPC ......... B01L 3/502753; B01L 3/502746; B01L 2200/16; B01L 2300/0681;
(Continued)

(56) References Cited

U.S. PATENT DOCUMENTS 9,464,319 B2 * 10/2016 Ismagilov ............... B01F 25/14
2017/0209864 A1 * 7/2017 Grisham ............ G01N 33/5094

FOREIGN PATENT DOCUMENTS

DE 10046173 A1 3/2002
DE 10313201 A1 10/2004
(Continued)

OTHER PUBLICATIONS

Han Wei Hou'\ Ali Asgar S. Bhagat\ Wong Cheng Leel Sha Huang\Jongyoon Han\Chwee Teck Lim, IVficrofluidic Devices for Blood Fractionation, Micromachines 2011, 2, 319-343 (Year: 2011).*
(Continued)

*Primary Examiner* — Patrick Orme
(74) *Attorney, Agent, or Firm* — Hudak, Shunk & Farine Co. LPA

(57) ABSTRACT

A microfluidic blood serum generator having a first port and a second port, between which there is formed a microfluidic structure, wherein the microfluidic structure has a supply duct communicating with the first port, a clotting region into which the supply duct discharges, and a discharge duct which communicates with the second port and into which the clotting region transitions, wherein the first port is designed to introduce a blood sample at a first pressure and the second port is designed to apply a second pressure that is lower than the first pressure, wherein the clotting region is formed by a single, coherent cavity, and wherein a barrier for retaining a clotted blood sample is arranged in the transition from the clotting region to the discharge duct. A
(Continued)

method for separating off blood serum from a blood sample using a blood serum generator of this kind.

22 Claims, 5 Drawing Sheets

(52) U.S. Cl.
CPC ... *B01L 2200/16* (2013.01); *B01L 2300/0681* (2013.01); *B01L 2400/0406* (2013.01); *B01L 2400/0487* (2013.01); *B01L 2400/086* (2013.01)

(58) Field of Classification Search
CPC ..... B01L 2400/0406; B01L 2400/0487; B01L 2400/086; B01L 2300/0663; G01N 33/491
See application file for complete search history.

(56) References Cited

FOREIGN PATENT DOCUMENTS

| DE | 102013012678 A1 | 2/2015 | | |
|---|---|---|---|---|
| DE | 102014214026 A1 | 1/2016 | | |
| DE | 102018111834 A1 | 11/2019 | | |
| WO | WO-2005058500 A1 | * | 6/2005 | ........ B01L 3/502746 |
| WO | 2014182844 A1 | 11/2014 | | |

OTHER PUBLICATIONS

Ritzi-Lehnert, M.; "Development of chip-compatible sample preparation for diagnosis of infectious diseases", Expert Rev. Mol. Diagn., 2012, pp. 189-206, vol. 12(2), ISSN 1473-7159; Expert Reviews Ltd.

Hou, H.; "Microfluidic Devices for Blood Fractionation", Micromachines, 2011, pp. 319-343, vol. 2, www.mdpi.com/journal/micromachines; ISSN 2072-666X; doi: 10.3390/mi2030319.

Becker, H.; "Highly Efficient On-Chip Plasma/Serum Generation for Disposable Point-of-Care Devices", 14th International Conference on Miniaturized Systems for Chemistry and Life Sciences, Oct. 3-7, 2010, Groningen, The Netherlands.

Bourzac, K.; Der Zehn-Minuten-Krebstest, Dec. 15, 2008 blog, Technology Review.

* cited by examiner

MICROFLUIDIC DEVICE AND METHOD FOR SEPARATING OFF BLOOD SERUM

FIELD OF THE INVENTION

The invention relates to a microfluidic structure, in particular a microfluidic blood serum generator, with a microfluidic structure for separating off blood serum from a blood sample. The invention further relates to a method for separating off blood serum from a blood sample by means of such a blood serum generator.

BACKGROUND OF THE INVENTION

A microfluidic device in the sense of this document is understood to be a component that is usually flat and typically about the size and shape of a credit card, in particular a microfluidic chip, whose base plate (also referred to as substrate) is made in particular of polymer, glass, or silicon, into which the microfluidic structure for separating blood serum and any further fluid channels and/or other microstructures, such as micropumps, actuators, sensors, membranes, valves, stirring elements, or the like are incorporated in a known manner by injection molding, hot stamping or milling. The microfluidic device, sometimes referred to as a "lab-on-a-chip," can be used generally for chemical synthesis or analysis as well as for medical diagnostics in the laboratory or in the field. Its miniaturization makes it particularly suitable for the synthesis and/or analysis of minute quantities of liquid.

Microfluidic devices and microfluidic structures are used to handle very small fluid quantities from a few ml to quantities within the µl range. The fluid channels in the microfluidic structures have lateral dimensions in the range of a few mm and smaller. Fluids are manipulated in such a microfluidic structure in a flow system. That is, by generating a pressure differential (positive pressure and/or vacuum) through the fluid channels between a first port and a second port of the microfluidic device. Devices for control or operation, for example, are connected to the microfluidic device, or it is inserted into them for this purpose. Manual operation is also possible.

Traditionally, blood serum is extracted from a blood sample in a laboratory by centrifuging the blood sample after clotting in a reaction tube so that the serum separates from the clotted, solid components of the blood. Since then, centrifugal microfluidic chips have also been developed for microfluidic-scale plasma collection (see, for example, Marion Ritzi-Lehnert et al. "Development of chip-compatible sample preparation for diagnosis of infectious diseases," Expert Review of Molecular Diagnostics 12:2, pp. 189-206 (2012)).

Another method for separating off blood serum from a blood sample makes use of a filtering process. WO 2014/182844 A1 is referred to for this. The known microfluidic device comprises a sample inlet connected to a microfluidic channel, wherein a composite membrane with filter elements is situated between the inlet and the microfluidic channel, the membrane being designed to receive the blood sample, hold it in place, initiate a blood clotting process, and selectively retain the clotted blood components while the liquid blood serum is withdrawn from the membrane and transported away through the microfluidic channel.

While centrifugation on a microfluidic scale requires additional equipment expenditure, blood separation methods using filter membranes are disadvantageous in that such filters have very small pore cross sections in order to retain blood cells, bacteria, or other particles. This not only poses the risk of clogging but also inhibits the flow. To compensate for this, the membranes usually have a large filter surface area and thus inevitably a large membrane capacity, which in turn makes it necessary to provide larger volumes of blood (in the range of several hundred µl) for analysis. Outfitting such microfluidic structures with membranes in a reliable manner also requires additional materials and installation steps.

Accordingly, the invention is based on the task of providing a microfluidic blood serum generator and a method for separating off blood serum from a blood sample that enables the reliable processing of very small, "patient-friendly" amounts of blood in the range of as little as 10 µl without increased equipment expenditure.

SUMMARY OF THE INVENTION

The task is solved by a microfluidic blood serum generator as well as by a method for using the blood serum generator. Further advantageous embodiments of the invention are given in the dependent patent claims.

The blood serum generator according to the invention comprises a microfluidic structure for separating off blood serum from a blood sample, the blood serum generator having a first port and a second port, between which the microfluidic structure is formed, the microfluidic structure having a supply duct communicating with the first port, a clotting region into which the supply duct discharges, and a discharge duct communicating with the second port, into which the clotting region transitions, wherein the first port is designed to introduce a blood sample at a first pressure and the second port is designed to apply a second pressure that is lower than the first pressure, wherein the clotting region is formed by a single, coherent cavity, and wherein a barrier for retaining a clotted blood sample is located in the transition from the clotting region to the discharge duct.

The method according to the invention for separating off blood serum from a blood sample comprises the following steps: Provision of a microfluidic blood serum generator having a microfluidic structure of the type described above; transportation of a blood sample from the supply duct to the clotting region, driven by a first pressure drop from the first port to the second port; retention of the blood sample in the clotting region until it is clotted; and transportation of the blood serum from the clotting region to the discharge duct, driven by a second pressure drop from the first port to the second port, while the remainder of the clotted blood sample is retained in the clotting region by means of the barrier, wherein the second pressure drop and the barrier in the transition from the clotting region to the discharge duct are designed such that intermolecular forces hold the remainder of the clotted blood sample together.

In contrast to filter-based blood separation processes, the invention is based on the knowledge that the remainder of the clotted blood sample, also called the cruor, has such strong intermolecular forces or adhesive forces that even when subjected to a pressure gradient within the microfluidic structure that is sufficient to extract the serum from this structure, and while it is retained by a barrier, it does not disintegrate, nor does it release intracellular components or blood cells (hemolysis) or dissolved erythrocytes that contaminate the blood serum. This process control is subsequently referred to as "clean extraction" for simplification of terminology.

In contrast to the membrane, which has a large number of pores in which the blood is distributed and clots, the inventors have realized that it is therefore sufficient to design the clotting region in the form of a single coherent cavity.

The cavity of the clotting region preferably does not exceed a volume of 50 µl and preferably does not exceed 25 µl.

A key positive effect is that the entire volume of the clotting region can be used efficiently, resulting in a very high yield of blood serum. The serum yield in the method according to the invention is between 10% and 25%, depending on the amount of whole blood. This allows for minimizing the volume of the clotting region. The volume of 50 µl or less ensures that a sufficient amount of serum can be provided for subsequent analysis, which requires only a few drops of blood from a patient. For volumes of 25 µl or less, even just one to two drops are sufficient for analysis.

Also preferred is that the barrier comprises a cross-sectional constriction, relative to a main flow direction, at the transition from the clotting region to the discharge duct.

The exact geometric structure of the barrier is not stipulated, provided that the barrier is suitable for retaining the cruor in the clotting region. This can be achieved, for example, by means of a cross-sectional taper. It can be step-shaped or ramp-shaped in the main flow direction. The latter variant has the advantage that the flow within the clotting region is more uniform, the cavity of the clotting region can be filled reliably, and no serum residues remain because there are no corners inhibiting proper flow in the area of the cross-sectional taper.

Alternatively or in addition to the cross-sectional constriction, the invention is further embodied in that the barrier comprises a lattice having no more than 10 passages for the blood serum.

Such a lattice is also suitable for retaining the cruor under the conditions of clean extraction. The maximum number of 10 passages ensures that the structure can be carved out of the microfluidic chip's substrate material as a part of the microfluidic structure by injection molding, hot stamping, or milling. This feature also serves to differentiate it from filter-based technology, in which the filter membrane is a separate element whose manufacture incurs further costs.

It has proven to be particularly advantageous that the barrier provides a minimum clear width perpendicular to the main flow direction at the transition from the clotting region to the discharge duct, the width being not less than 10 µm, preferably not less than 50 µm, and not more than 200 µm, preferably not more than 150 µm.

Due to manufacturing limitations, the fluidic channels of fluidic structures, and thus also those of the supply duct, the clotting region, and the discharge duct, are essentially rectangular in shape. With this geometry, the minimum clear width is understood to be the smaller of the wall distances. The above dimensions, whether in a cross-sectional taper or in the passages between the grids of a lattice, have been shown to securely retain the cruor while providing sufficient flow area for withdrawing the blood serum from the clotting region.

Particularly preferred is an embodiment in which the barrier comprises a shallow channel section having a clear height of not less than 10 µm, preferably not less than 50 µm, and not more than 200 µm, preferably not more than 150 µm.

Also preferred is that the barrier comprise a lattice having a grid spacing of not less than 50 µm and not more than 350 µm, preferably not more than 300 µm.

The barrier can be formed on its own or in conjunction with the lattice or the cross-sectional constriction, wherein the cross-sectional constriction can be followed by the shallow channel section. In the latter case, the lattice is preferably located in the shallow channel section.

Particularly preferably, a clot activator, especially a soluble or gel clot activator, is introduced into the clotting region.

Although the clot activator is not instrumental in achieving the extraction of blood serum according to the invention, it accelerates the process of clotting the fresh blood from a few minutes to 10 to 20 seconds. The advantage is therefore a considerable time savings for the full extraction process.

The clot activator preferably fills the clotting region in the form of a porous structure.

The pores provide the capacity for the fresh blood. The clot activator exhibiting the most uniform distribution and the largest pore surface area possible ensures that the clot activator dissolves quickly in the blood and that the blood clots at a uniform rate.

Procedurally, the clot activator is provided in the clotting region to accelerate the clotting process prior to use of the blood serum generator according to the invention, and particularly preferably by introducing the clot activator as a solution into the clotting region of the microfluidic structure and subsequently freeze-drying it by cooling and evacuation in the open microfluidic structure. "Open" refers here to a variant in which the ports of the microfluidic structure are at least partially unoccupied to allow water to escape from the microfluidic structure during freeze drying. Another variant involves introducing and freeze-drying the clot activator before covering the chip in which the microfluidic structure is incorporated (that is, before covering the microfluidic structure in the substrate with a film) and then covering the chip.

The clot activator ideally dissolves in the blood sample completely when the blood sample is transported to the clotting region and/or when the blood sample is retained in the clotting region, so that—with the exception of solid components of blood-no solid components remain in the clotting region. The clot activator is therefore not a structural component of the blood serum generator and so, unlike a filter membrane, does not serve to retain the cruor, but rather is a constituent of it.

Preferably, the volume ratio of clot activator to fresh blood within the clotting region is 1:3 to 1:5, particularly preferably 1:4.

The method is further advantageously embodied in that the barrier comprises a shallow channel section, and the clotting process in the shallow section is monitored optically. In particular, the shallow channel section can have the clear height specified above.

Optical monitoring can occur regardless of whether a clot activator is introduced or not. It can be used to determine the clotting factors as well as to control the subsequent processes. For example, movements can be detected via speckle imaging. In particular, the transport of the blood serum out of the clotting region is thus advantageously initiated as soon as cessation of movement is detected in this manner during optical monitoring of the clotting process. This is because it is then assumed that the blood particles are effectively no longer moving, and the clotting process is considered complete.

The method according to the invention is further advantageously embodied in that the first pressure drop from the first port to the second port is less than 10 mbar, preferably less than 5 mbar. The vacuum should not be higher than 10 mbar, better still not higher than 5 mbar, as uncontrolled separation and/or splitting of the drop of blood can otherwise occur.

Preferably, the second pressure drop from the first port to the second port is less than 25 mbar, particularly preferably less than 15 mbar.

It has been shown that even at these small pressure differentials, the blood serum can be drawn out of the cruor. The pressure differentials are, however, so small that a reliable (i.e., without destroying the cruor, especially without hemolysis), clean extraction is achieved.

In a preferred embodiment of the microfluidic structure, the first port comprises a receiving bore for a capillary tube or is itself designed as a capillary tube.

A capillary tube is suitable for collecting a drop of blood, for example from a patient's finger via capillary action, until the capillary is completely filled. Furthermore, such a capillary tube has a defined volume, thereby introducing a fixed amount of blood into the microfluidic structure. This volume is preferably dimensioned according to the measurements of the microfluidic structure such that the cross section of the clotting region is completely filled. A preferred volume of such a capillary tube is 20 µl, which approximately corresponds to one drop of blood. Such a capillary tube can then be inserted in a leak-tight manner into the receiving bore of the first port so that the pressure drop from the first port to the second port ensures that the capillary is emptied and the blood is drawn into the clotting region via the supply duct.

Particularly preferably, this happens because of a vacuum applied to the second port. This is the simplest solution from the standpoint of process technology for generating both the first and second pressure drops. The open end of the capillary tube inserted into the receiving bore then simply remains exposed to ambient pressure and does not need to be connected to a pressure line.

In another advantageous embodiment of the method, retention of the blood sample in the clotting region is achieved by equalizing the first pressure drop once the blood sample has reached a designated position within the microfluidic structure.

Particularly preferably, the blood sample in the microfluidic structure forms a continuous fluid plug with a front boundary, wherein arrival of the front boundary at the designated position is detected by a sensor.

Also preferred is the optical or capacitive detection of the arrival of the front boundary at the designated position.

Alternatively, the arrival of the front boundary at the designated position can also be detected by a differential pressure measurement in the form of an increased pressure differential between the first port and the second port, if a cross-sectional constriction is provided at the designated position.

Therefore, the designated position is advantageously located in the area of the barrier at the transition between the clotting region and the discharge duct, particularly preferably in the shallow channel section of the barrier.

BRIEF DESCRIPTION OF THE DRAWINGS

Further advantages and features of the invention are explained below with reference to the figures. The following are shown.

DETAILED DESCRIPTION OF THE INVENTION

For the purpose of describing the geometry of the microfluidic structures, the term "fluid flow" is used below for simplification to denote the flow of fresh blood, serum, or any other fluid in the microfluidic structure. "Flow direction" refers in any case to the main flow direction prevailing in a component, which approximately follows the contour of the respective microfluidic structure. "Lateral" refers to the direction perpendicular to the direction of flow in the main plane of the blood serum generator.

Figure 1:
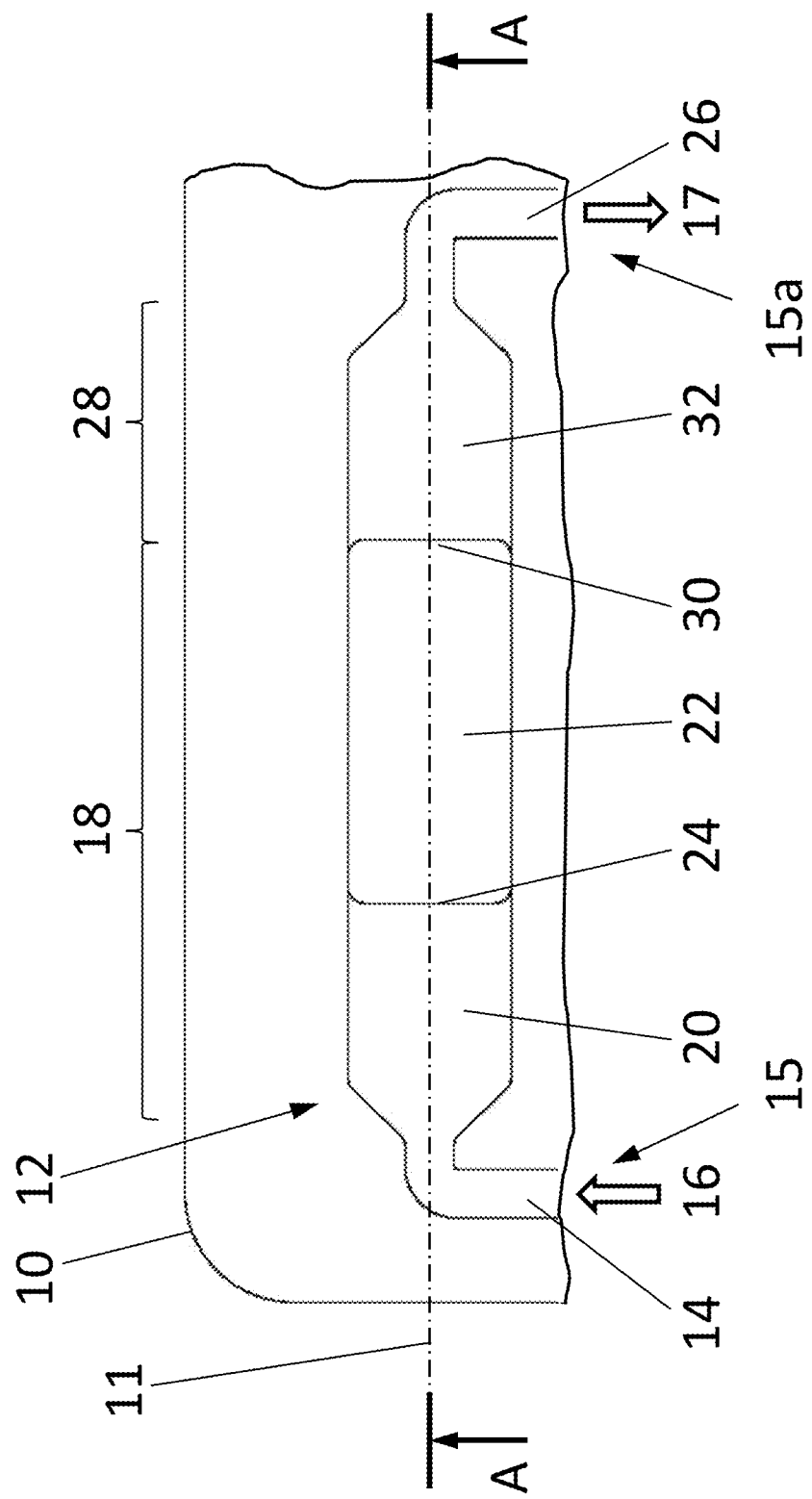
FIG. 1 shows a section of a first embodiment of the microfluidic blood serum generator according to the invention in top view.
Figure 2:
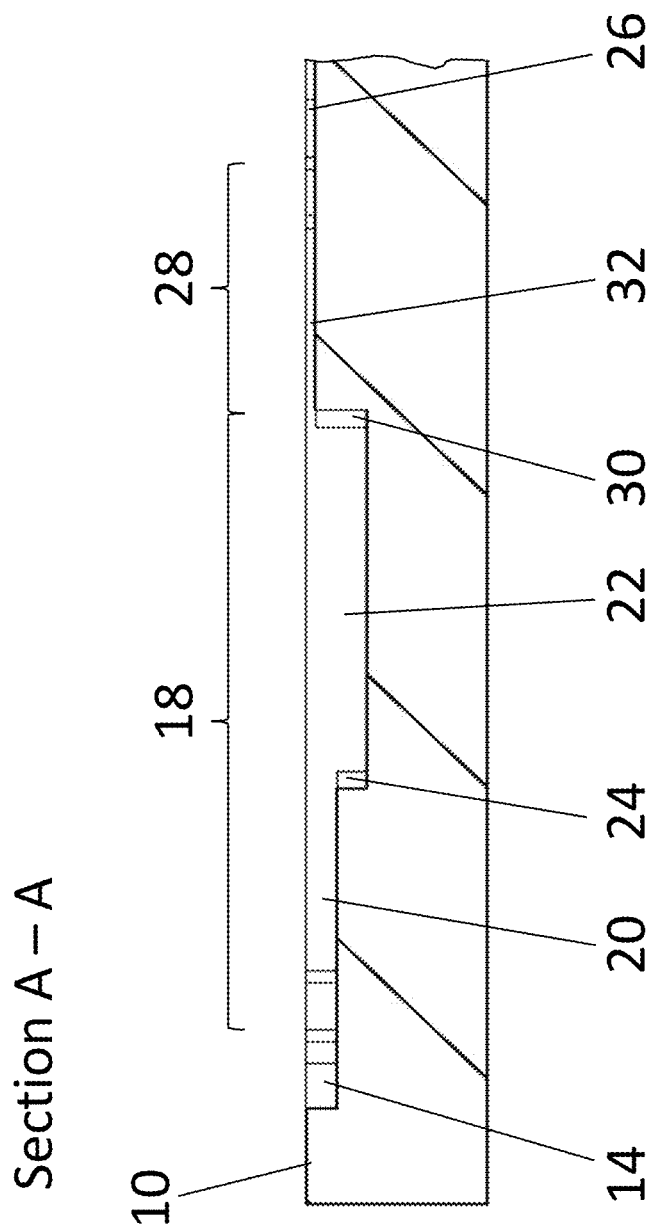
FIG. 2 shows the embodiment according to FIG. 1 in sectional view from the side.

FIGS. 1 and 2 depict two views of a first embodiment of the microfluidic blood serum generator 10 according to the invention. FIG. 1 shows the top view of the main plane of the flat substrate, which has the shape of a credit card, of this microfluidic device. FIG. 2 ("Section A-A") shows a section through this substrate along section line 11 from the perspective indicated by the arrows "A."

The blood serum generator 10 has a microfluidic structure 12, and only the section of the microfluidic structure 12 relevant to the separation of blood serum from a blood sample is shown in the figures. In the direction of flow, indicated by arrows 16 and 17, in front of and/or behind the section of the microfluidic structure 12 shown, there could be further microfluidic structure components, such as micropumps, actuators, sensors, membranes, valves, stirring elements, mixers, reaction chambers, and the like for preparation and/or analysis of the sample. At least two ends of the overall microfluidic structure exhibit a first port 15 and a second port 15*a* to allow a pressure gradient to be generated across them within the microfluidic structure.

The relevant microfluidic structure 12 comprises a supply duct 14 into which fresh blood flows from a first port (not shown) in the direction of flow indicated by arrow 16. The supply duct 14 opens into a clotting region 18, into which the blood flows and where it is retained for the purpose of clotting. The clotting region 18 is in turn divided into an inlet region 20, which laterally widens the fluid flow from the cross section of the supply duct 14, and a deep region 22 downstream, the inlet region 20 being shallower than the deep region 22. The transition between them, edge 24, is executed as a step.

The clotting region 18 transitions to a discharge duct 26, with a barrier being located in the transition 28 from the clotting region 18 to the discharge duct 26. The barrier comprises an edge or a stepped cross-sectional constriction 30 and an adjoining shallow channel section 32, which laterally constricts the fluid flow all at once to the width of the discharge duct 26. The channel after the last element of the barrier in the direction of flow is designated the discharge duct 26'.

Fresh blood is transported as a fluid plug (that is, a cohesive, finite volume), driven by a first pressure drop from the first port to the second port, from the supply duct 14 to the clotting region 18, initially filling the inlet region 20 as the blood fluid plug spreads laterally. The blood then flows over the edge 24 into the deep region 22 until this is completely filled. The transport is then stopped when a front boundary of the fluid plug is detected by a sensor at a designated position in the area of the barrier (that is, in transition 28). This preferably occurs in an area of the transition as far downstream as possible in order to minimize the volume that must be filled with serum upstream of the discharge duct after clotting. For this purpose, a light curtain or a sensor according to DE 10 2014 214 026 A1, for example, could be set up, which optically or electrically monitors the shallow channel section 32. When a light curtain is used for the sensor, as soon as the blood arriving there absorbs the light from the light curtain, the pressure drop from the first to the second port is equalized. In other words, a vacuum applied preferably to the second port for generation of the pressure drop is turned off, or the second port is vented, so that the blood stops instantaneously.

The fluid plug is retained in this position until the blood in the clotting region 18 has clotted completely. Clotting may be accelerated by a clot activator having been located in the clotting region 18 beforehand, particularly preferably in the deep region 22. Clotting is preferably monitored optically. This also preferably occurs in the shallow channel section 32 of the transition 28 or, alternatively, the shallow inlet region 20 of the clotting region 18.

Figure 3:
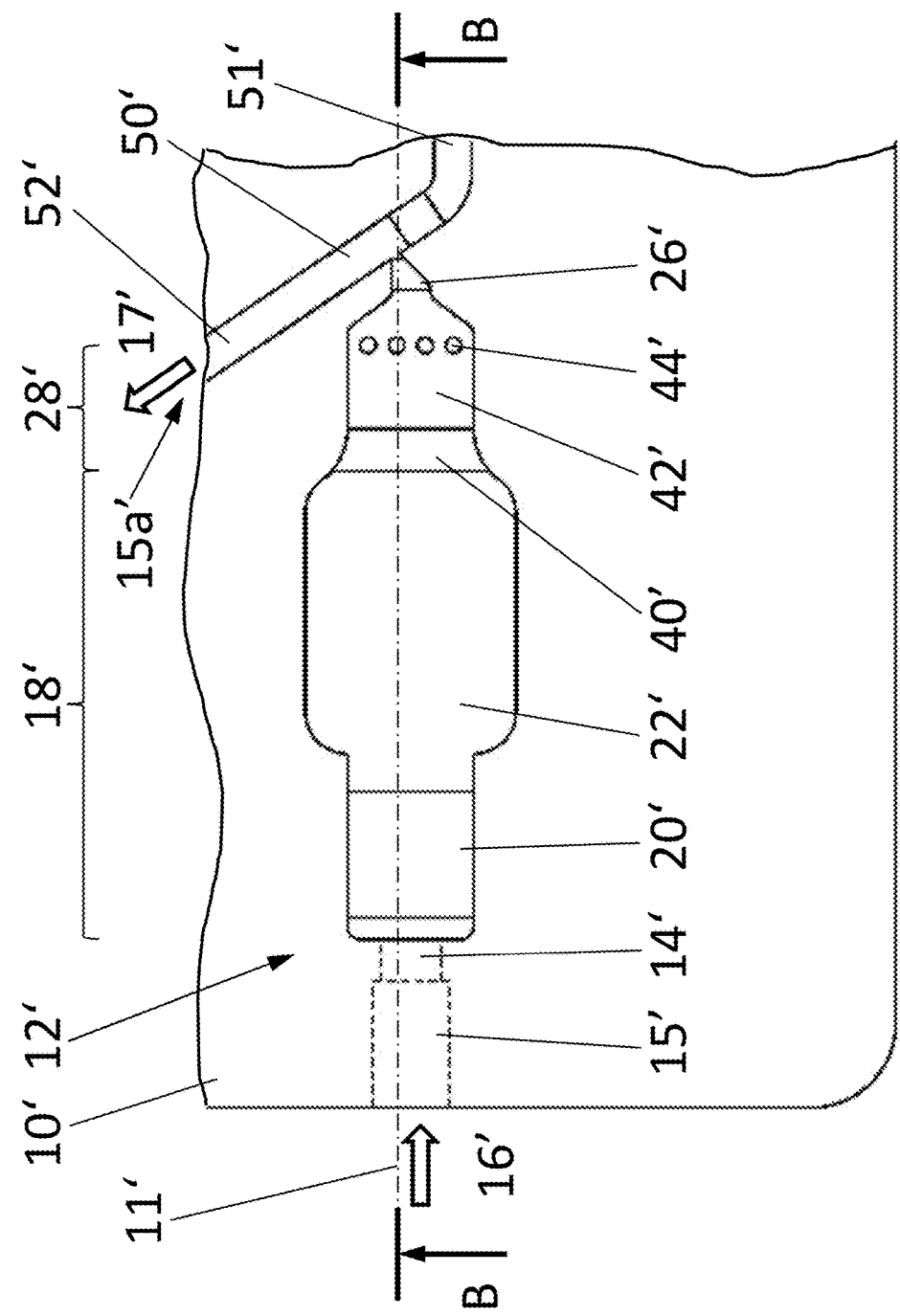
FIG. 3 shows a section of a second embodiment of the microfluidic blood serum generator according to the invention in top view.
Figure 4:
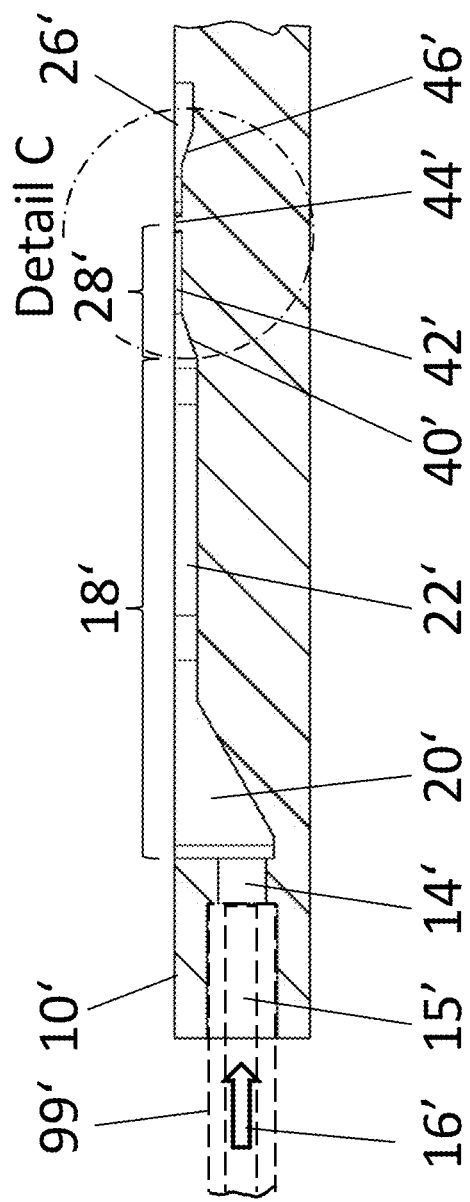
FIG. 4 shows the embodiment according to FIG. 3 in sectional view from the side.
Figure 5:
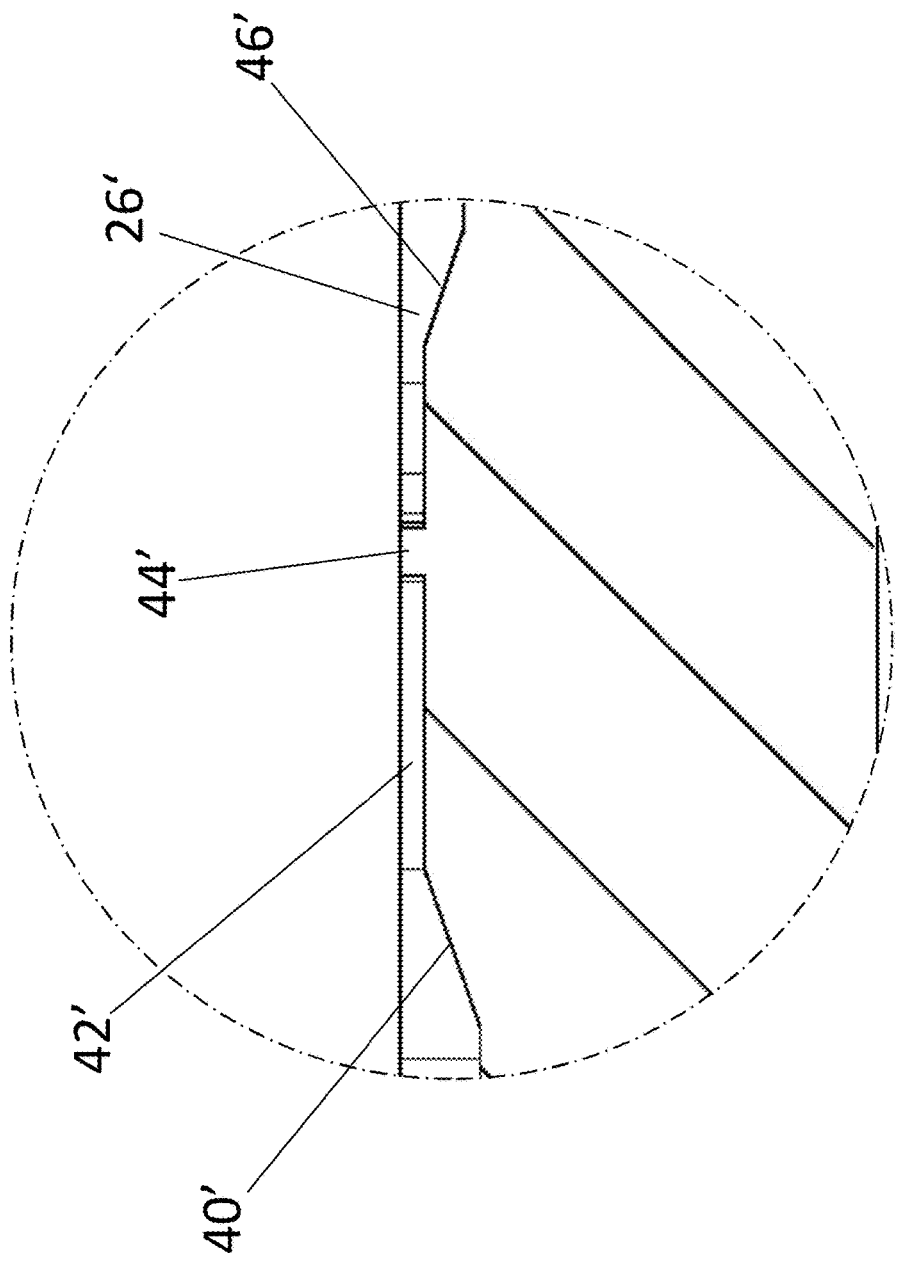
FIG. 5 shows an enlargement of a section of FIG. 4.

A second embodiment of the microfluidic blood serum generator 10' according to the invention is explained with reference to FIGS. 3 to 5. FIG. 3 shows again a top view of the main plane of the flat substrate, which has the shape of a credit card, of the microfluidic device. FIG. 4 ("Section B-B") shows a section through this substrate along section line 11' from the perspective indicated by the arrows "B". FIG. 5 ("Detail C") shows an enlarged section of FIG. 4 at the circle in FIG. 4 that is labeled identically.

The blood serum generator 10' has a microfluidic structure 12', wherein again only the section of the microfluidic structure 12' relevant to the separation of blood serum from a blood sample is shown in the figures, along with an adjacent analysis channel 50'. In the direction of flow, indicated by arrows 16' and 17', there could again be further microfluidic structure components, such as micropumps, actuators, sensors, membranes, valves, stirring elements, mixers, reaction chambers, and the like for preparation and/or analysis of the sample.

The relevant microfluidic structure 12' comprises a supply duct 14' into which fresh blood flows from a first port 15' in the direction of flow indicated by arrow 16'. The first port 15' has a cylindrical bore edgewise in the substrate of the blood serum generator 10', the bore being designed to receive a capillary tube 99' in a leak-tight manner.

The supply duct 14' opens into a clotting region 18', into which the blood flows and where it is retained for the purpose of clotting. The clotting region 18' is again divided into an inlet region 20', which laterally expands the fluid flow from the cross section of the supply duct 14'. In contrast to the first embodiment, the inlet region 20' is deep on the inlet side and tapers like a ramp in the downstream direction to the depth of an adjoining shallow region 22' of the clotting region 18'. The reason for this geometry is the lower-lying first port 15', from which there must be a transition into a surface channel. In the shallow region 22', the clotting region 18' is again laterally widened compared to the inlet region 20' in order to provide sufficient volume for the blood sample and, if necessary, a clot activator.

The clotting region 18' again transitions to a discharge duct 26', the transition 28' this time having a barrier that comprises a cross-sectional constriction in the form of a ramp 40', a shallow channel section 42' which again laterally constricts the fluid flow at the end to the width of the discharge duct 26', and a lattice 44' with a total of five passages for the blood serum.

The channel after the last element of the barrier in the direction of flow is designated the discharge duct 26'. The discharge duct 26' initially continues at the same depth as the shallow channel section 42' of the barrier and then widens in the depth direction in the form of a ramp 46' as it continues to heavily constrict the fluid flow laterally. This is a particularly favorable feature because the discharge duct has a very small volume so that the blood serum can be made available as directly as possible without loss to further processing. The discharge duct 26' finally opens downstream into the analysis channel 50', in which the collected serum is transported further via a pressure gradient applied between an inlet side 51' and an outlet side 52' of the analysis channel 50' in the direction of arrow 17'. This decouples the microfluidic structure 12' from the rest of the process and prevents contamination of the analysis channel 50' with other blood components.

Fresh blood is also transported here in the form of a fluid plug, driven by a first pressure drop from the first port 15' to a second port 15a', from the supply duct 14' to the clotting region 18', initially filling the inlet region 20' as the blood fluid plug spreads laterally. The blood then flows over the ramp of the inlet region 20' into the shallow region 22' until this is completely filled. The transport is again then stopped when a front boundary of the fluid plug is detected by a sensor at a designated position in the area of the barrier (that is, in transition 28'). This preferably occurs in an area of the transition as far downstream as possible in order to minimize the volume that must be filled with serum upstream of the discharge duct after clotting. A light curtain could be used for this purpose, as described above. Alternatively, the arrival of the front boundary of the fluid plug at the lattice 44' can be detected by a differential pressure measurement in the form of an increased pressure differential between the first port and the second port, because overcoming itself requires additional work due to boundary layer effects, which is detectable as a differential pressure increase in the system.

The fluid plug is retained in this position until the blood in the clotting region 18' has clotted completely. Clotting may be accelerated by a clot activator having been located in the clotting region 18' beforehand, particularly preferably in the shallow region 22'. Again, clotting is preferably monitored optically.

The research that led to these results was funded by the European Union.

REFERENCE LIST 10, 10' blood serum generator
11, 11' section line
12, 12' microfluidic structure
14, 14' supply duct
15, 15' first port
15a, 15a' second port
16, 16' flow direction arrow
17, 17' flow direction arrow
18, 18' clotting region
20, 20' inlet region of the clotting region
22 deep region of the clotting region
22 shallow region of the clotting region
24 edge
26, 26' discharge duct
28, 28' transition
30 edge, or step-shaped cross-sectional constriction
32 shallow channel section
40' cross-sectional constriction in ramp form
42' shallow channel section
44' lattice 46' discharge duct ramp
50' analysis channel
51' inlet side
52' outlet side
99 capillary tube

What is claimed is:

1. A microfluidic blood serum generator, comprising: a microfluidic structure, the blood serum generator having a first port and a second port, between which the microfluidic structure is formed,
the microfluidic structure having a supply duct communicating with the first port, a clotting region into which the supply duct discharges, and a discharge duct communicating with the second port and into which the clotting region transitions,
the first port being designed to introduce a blood sample under a first pressure and the second port being designed to apply a second pressure that is lower than the first pressure,
the clotting region being formed by a single, coherent cavity,
wherein a barrier for retaining a clotted blood sample is situated in a transition from the clotting region to the discharge duct, and
wherein the cavity of the clotting region does not exceed a volume of 50 µl.

2. The microfluidic blood serum generator according to claim 1, wherein the barrier comprises a cross-sectional constriction as viewed in a main flow direction in the transition from the clotting region to the discharge duct.

3. The microfluidic blood serum generator according to claim 1, wherein the barrier comprises a lattice with no more than 10 passages for the blood serum.

4. The microfluidic blood serum generator according to claim 1, wherein the barrier provides a minimum clear width in a direction perpendicular to a main flow direction in the transition from the clotting region to the discharge duct, the minimum clear width being not less than 10 µm and not more than 200 µm.

5. The microfluidic blood serum generator according to claim 1, wherein the barrier comprises a channel section having a clear height of not less than 10 µm and not more than 200 µm.

6. The microfluidic blood serum generator according to claim 1, wherein the barrier comprises a lattice having a grid spacing of not less than 50 µm and not more than 350 µm.

7. The microfluidic blood serum generator according to claim 1, wherein a clot activator is introduced into the clotting region.

8. The microfluidic blood serum generator according to claim 7, wherein the clot activator at least partially fills the clotting region in the form of a porous structure.

9. The microfluidic blood serum generator according to claim 1, wherein the first port comprises a receiving bore for a capillary tube or is formed as a capillary tube.

10. A method for separating off blood serum from a blood sample comprising the following steps:
obtaining a blood serum generator with a microfluidic structure according to claim 1,
driving transportation of a blood sample from the supply duct to the clotting region by a first pressure drop from the first port to the second port,
retaining the blood sample in the clotting region until it has clotted, and
driving transportation of the blood serum from the clotting region to the discharge duct, by a second pressure drop from the first port to the second port, while retaining the remainder of the clotted blood sample in the clotting region by means of the barrier,
wherein the second pressure drop and the barrier in the transition from the clotting region to the discharge duct are designed such that intermolecular forces hold the remainder of the clotted blood sample together.

11. The method according to claim 10, further including providing a clot activator in the clotting region to accelerate the clotting process.

12. The method according to claim 11, wherein the clot activator is introduced as a solution into the clotting region and subsequently freeze-dried in the open microfluidic structure.

13. The method according to claim 11, wherein the clot activator dissolves itself in the blood sample when the blood sample is transported into the clotting region and/or when the blood sample is retained in the clotting region.

14. The method according to claim 10, wherein the barrier comprises a channel section, and the clotting process in the channel is monitored optically.

15. The method according to claim 10, wherein the first pressure drop from the first port to the second port is less than 10 mbar.

16. The method according to claim 10, wherein the second pressure drop from the first port to the second port is less than 25 mbar.

17. The microfluidic blood serum generator according to claim 1, wherein the barrier comprises a cross-sectional constriction as viewed in a main flow direction in the transition from the clotting region to the discharge duct, wherein the barrier comprises a lattice with no more than 10 passages for the blood serum, and wherein the barrier provides a minimum clear width in a direction perpendicular to a main flow direction in the transition from the clotting region to the discharge duct, the minimum clear width being not less than 50 µm, and not more than 150 µm.

18. The microfluidic blood serum generator according to claim 17, wherein the barrier comprises a channel section having a clear height of not less than 50 µm and not more than 150 µm, wherein the barrier comprises a lattice having a grid spacing of not less than 50 µm and not more than 300 µm, and wherein a clot activator is introduced into the clotting region.

19. The microfluidic blood serum generator according to claim 18, the clot activator at least partially fills the clotting region in the form of a porous structure, and wherein the first port comprises a receiving bore for a capillary tube or is formed as a capillary tube.

20. A microfluidic blood serum generator, comprising:
a microfluidic structure, the blood serum generator having a first port and a second port, between which the microfluidic structure is formed,
the microfluidic structure having a supply duct communicating with the first port, a clotting region into which the supply duct discharges, and a discharge duct communicating with the second port and into which the clotting region transitions,
the first port being designed to introduce a blood sample under a first pressure and the second port being designed to apply a second pressure that is lower than the first pressure,
the clotting region being formed by a single, coherent cavity,
wherein a barrier for retaining a clotted blood sample is situated in a transition from the clotting region to the discharge duct, and wherein the barrier comprises a channel section having a height of not less than 10 μm and not more than 200 μm which laterally constricts the fluid flow to the width of the discharge duct.

21. The microfluidic blood serum generator according to claim 20, wherein the discharge duct is arranged to further laterally constrict the fluid flow.

22. A microfluidic blood serum generator, comprising:
a microfluidic structure, the blood serum generator having a first port and a second port, between which the microfluidic structure is formed,
an analysis channel having an inlet side and an outlet side,
the microfluidic structure having a supply duct communicating with the first port, a clotting region into which the supply duct discharges, and a discharge duct communicating with the second port and into which the clotting region transitions,
the first port being designed to introduce a blood sample under a first pressure and the second port being designed to apply a second pressure that is lower than the first pressure,
the clotting region being formed by a single, coherent cavity,
wherein a barrier for retaining a clotted blood sample is situated in a transition from the clotting region to the discharge duct, and
wherein the discharge duct opens downstream into the analysis channel between the inlet side and the outlet side.

* * * * *